United States Patent
Salden

(10) Patent No.: US 10,684,283 B2
(45) Date of Patent: Jun. 16, 2020

(54) METHOD FOR THE SEROLOGICAL DIAGNOSIS OF RHEUMATOID ARTHRITIS

(71) Applicant: Novio TH B.V., Rotterdam (NL)

(72) Inventor: Martinus Hubertus Leonardus Salden, Nijmegen (NL)

(73) Assignee: NOVIO TH B.V., Rotterdam (NL)

( * ) Notice: Subject to any disclaimer, the term of this patent is extended or adjusted under 35 U.S.C. 154(b) by 0 days.

(21) Appl. No.: 15/307,475

(22) PCT Filed: Apr. 22, 2015

(86) PCT No.: PCT/EP2015/058738
§ 371 (c)(1),
(2) Date: Oct. 28, 2016

(87) PCT Pub. No.: WO2015/169602
PCT Pub. Date: Nov. 12, 2015

(65) Prior Publication Data
US 2017/0052179 A1  Feb. 23, 2017

(30) Foreign Application Priority Data

May 5, 2014  (EP) .................................... 14166985

(51) Int. Cl.
| G01N 33/53 | (2006.01) |
| G01N 33/564 | (2006.01) |
| C07K 16/28 | (2006.01) |
| G01N 33/80 | (2006.01) |

(52) U.S. Cl.
CPC ....... *G01N 33/564* (2013.01); *C07K 16/2896* (2013.01); *G01N 33/80* (2013.01); *C07K 2317/40* (2013.01); *G01N 2333/70596* (2013.01); *G01N 2800/102* (2013.01)

(58) Field of Classification Search
CPC .. G01N 33/564; G01N 2440/18; G01N 33/80; G01N 2333/70596; G01N 2800/102; G01N 33/53; C07K 16/2896; C07K 2317/40
See application file for complete search history.

(56) References Cited

U.S. PATENT DOCUMENTS

| 5,413,913 | A | * | 5/1995 | Hillyard | ............... | G01N 33/531 |
| | | | | | | 435/2 |
| 2011/0008910 | A1 | | 1/2011 | Van Boekel et al. | | |
| 2012/0329072 | A1 | * | 12/2012 | Weber | ................ | G01N 33/6842 |
| | | | | | | 435/7.6 |

FOREIGN PATENT DOCUMENTS

| WO | 03050542 A2 | 6/2003 |
| WO | 03050542 A3 | 12/2003 |
| WO | 2008000714 A1 | 1/2008 |
| WO | 2009115612 A1 | 9/2009 |
| WO | 2013156377 A1 | 10/2013 |
| WO | 2014023957 A2 | 2/2014 |
| WO | 2015169602 A1 | 11/2015 |

OTHER PUBLICATIONS

Conrad et al. Autoantigens, Autoantibodies, Autoimmunity 2007;vol. 5, pp. 369-388.*
Fortenfant, Scand. J. Immunol. 49, 88-95, 1999.*
Colman et al., Res Immunol. Jan. 1994;145(1):33-6.*
Lerner et al., Nature 1982; 299:592-596, see p. 595-596.*
Routsias Rheumatology 2011;50:1189_1193.*
Hu et al., Proteomics 2011, 11, 1499-1507, p. 1501, left column; (Year: 2011).*
Catimel et al., Kinetics of the autologous red cell agglutination test, Journal of Immunological Methods, Oct. 15, 1993, pp. 183-192, vol. 165, No. 2, Elsevier Science Publishers B.V., Amsterdam, NL.
Schellekens et al., Citrulline is an essential constituent of antigenic determinant recognized by rheumatoid arthritis-specific autoantibodies, Journal of Clinical Investigation, Jan. 1, 1998, pp. 273-281, vol. 101, No. 1, American Society for Clinical Investigation, US.
Van Venrooij et al., Anti-CCP antibodies: the past, the present and the future, Nature Reviews Rheumatology, Jun. 7, 2011, pp. 391-398, vol. 7, No. 7.
Van Beers et al., ACPA fine-specificity profiles in early rheumatoid arthritis patients do not correlate with clinical features at baseline or with disease progression, Arthritis Research and Therapy, Oct. 1, 2013, p. R140, vol. 15, No. 5, Biomed Central, London, GB.
PCT International Search Report and Written Opinion, PCT/EP2015/058738 dated Jul. 6, 2015.
PCT International Preliminary Report on Patentability, PCT/EP2015/058738, dated Nov. 8, 2016.
Nachat et al. "Peptidylarginine Deiminase Isoforms 1-3 Are Expressed in the Epidermis and Involved in the Deimination of K1 and Filaggrin," The Society for Investigative Dermatolology, Feb. 2, 2005, 384-393 pp.

(Continued)

*Primary Examiner* — Julie Wu
*Assistant Examiner* — Carmencita M Belei
(74) *Attorney, Agent, or Firm* — Patent Law Works, LLP

(57) ABSTRACT

This disclosure relates to the field of diagnostic methods. A new marker antibody for rheumatoid arthritis, as well as a new method for detecting rheumatoid arthritis, is disclosed herein. Also provided herein are means and methods for predicting whether a subject will develop rheumatoid arthritis. This disclosure is based on the discovery that patients with rheumatoid arthritis have antibodies in their circulation that react specifically with citrullinated antibodies. In one aspect, the disclosure, therefore, relates to an antibody comprising a citrulline residue. In another aspect, the disclosure provides a method for the detection of antibodies specific for rheumatoid arthritis in a sample from a subject, wherein the sample is contacted with a citrullinated antibody and wherein it is determined whether the sample comprises antibodies specifically reactive with the citrullinated antibody.

20 Claims, 1 Drawing Sheet

(56) References Cited

OTHER PUBLICATIONS

Japanese Intellectual Patent Office, Notice of Reason of Refusal, Japanese Patent Application No. 2017-510743, pg 3 of translated copy dated December 30, 2018, 12 pages with translation.
"Antibody monoclonal anti-B WAKO for ABO type blood type kit anti-B blood grouping" package leaflet, Wako Pure Chemical Industries and Apr. 2014 (document in which a technical common sense is shown). http://www.pmda.go.jp/PmdaSearch/ivdDetail/890027_20200EZZ00114000_A_01_03#CONTRAINDICATION-AND-PROHIBITIONS Translation from Google Translate, 10 pages.

* cited by examiner

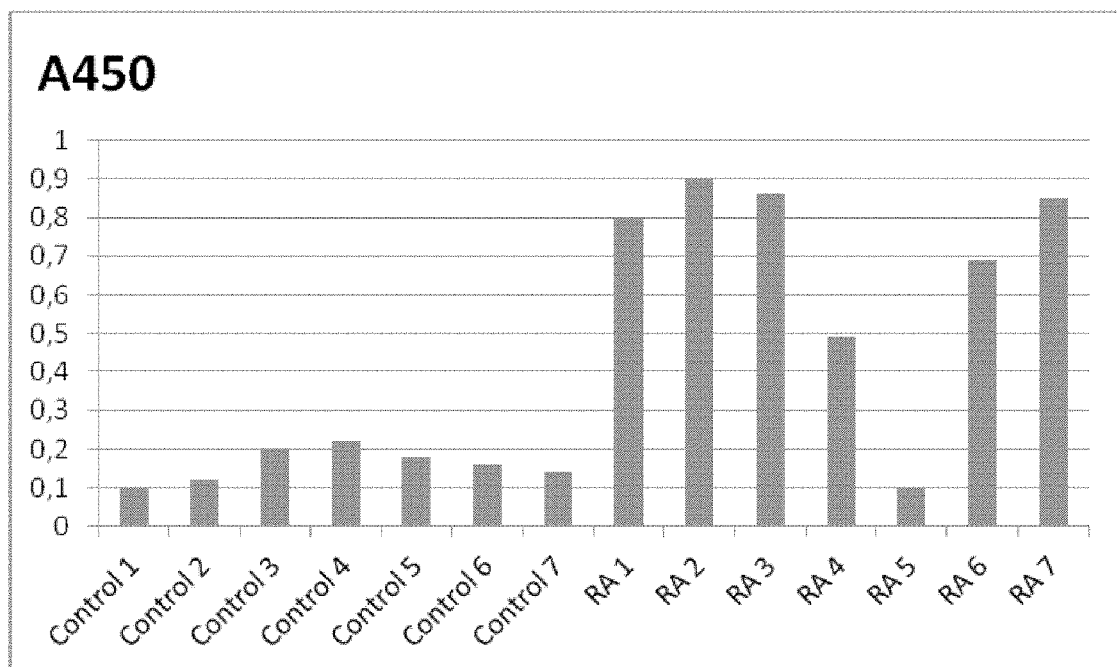

METHOD FOR THE SEROLOGICAL DIAGNOSIS OF RHEUMATOID ARTHRITIS

CROSS-REFERENCE TO RELATED APPLICATIONS

This application is a national phase entry under 35 U.S.C. § 371 of International Patent Application PCT/EP2015/058738, filed Apr. 22, 2015, designating the United States of America and published in English as International Patent Publication WO 2015/169602 A1 on Nov. 12, 2015, which claims the benefit under Article 8 of the Patent Cooperation Treaty to European Patent Application Serial No. 14166985.3, filed May 5, 2014.

TECHNICAL FIELD

This disclosure is in the field of diagnostic methods. A new marker antibody for rheumatoid arthritis is disclosed as well as a new method for detecting rheumatoid arthritis. Also disclosed are means and methods for predicting whether a subject will develop rheumatoid arthritis. The disclosure is based on the discovery that patients with rheumatoid arthritis have antibodies in their circulation that react specifically with citrullinated antibodies.

BACKGROUND

Serological diagnostic testing is of growing importance in the early detection and differentiation of rheumatoid arthritis (RA). Apart from the traditional detection of the rheumatoid factor, new specific autoantibodies to citrullinated antigens have made a crucial contribution to the diagnosis of RA.[26]

The rheumatoid factor is an autoantibody, which may be IgM, IgG or IgA, and first mentioned in 1922.[1] It recognizes domains CH2 and CH3 of the Fc segment of human IgG and is a component of the classification criteria for RA published by the American College of Rheumatology.[2]

Rheumatoid factor (RF) can be determined by various test methods; ELISA (enzyme-linked immunosorbent assay) and nephelometry are standardized methods. The mean specificity of detection of RF is about 79%, with sensitivity of about 60%.[3] In recent years, new autoantibodies have been detected and characterized in the sera of RA patients. These exhibit higher specificity and can, therefore, help to improve serological diagnostic testing.

One of the most important serological discoveries in rheumatology in recent years has been the characterization of autoantibodies directed against citrullinated filaggrin.[4] The starting point for this discovery was the identification of the target antigen for anti-keratin antibodies (AKA). These were first described in 1979 and are highly specific for RA.[4]

The target antigen filaggrin is only expressed in epithelial cells and not in joints or other organs; the pathogenetic significance of this finding was, therefore, initially unclear. Schellekens et al.[6] showed that only citrullinated forms of filaggrin were recognized by AKA.

Filaggrin may be citrullinated by enzymatic deimination of arginine residues to give citrulline residues. Citrullination is a post-translational modification, which alters the charge of a protein, leading to changes in its three-dimensional structure, which, in turn, results in changes in antigenic properties.[7] Citrullination has an essential physiological and biochemical role in cell differentiation and in programmed cell death (apoptosis).

First generation ELISAs for the detection of anti-citrullinated filaggrin showed a specificity for RA of about 85%, with sensitivity of 65% to 70%. Second generation ELISAs used synthetic peptides as antigen, with a ring structure due to intramolecular disulfide bridge formation. Use of these cyclic citrullinated peptides (CCP) has improved the specificity to between 96% and 98%, without changing the sensitivity.[8]

Several studies have now shown that anti-CCP antibodies are not only highly specific, but also of high predictive value for an erosive course of the disease and are thus of prognostic value.[9]

Studies with citrullinated peptide derivatives of fibrin and fibrinogen have now shown a cross-reaction between filaggrin and citrullinated fibrin.[12] Some publications have found high diagnostic specificity and sensitivity for the detection of anti-citrullinated fibrinogen antibodies in patients with RA.[13] With ELISA, the sensitivity for RA was about 75%, with specificity of 98%.

Another interesting citrullinated autoantigen is the citrullinated form of alpha-enolase, an enzyme that plays a role in glycolysis.[15] Citrullinated alpha-enolase has been detected—together with other citrullinated antigens—in the synovial tissue of patients with rheumatoid arthritis.[16]

Citrullinated vimentin has been described as a relevant autoantigen expressed in synovial tissue. Subsequently, it was clarified that citrullinated vimentin is identical to the formerly known antigen Sa, which stands for Savoie, the name of the patient in whom the respective autoantibody response was first identified. Anti-Sa antibodies provide a high specificity of >98%, but a limited sensitivity of 22% to 40% for patients with rheumatoid arthritis.[17]

An ELISA based on mutated citrullinated vimentin (MCV) has been commercially available for the diagnosis of rheumatoid arthritis for some time and has about the same diagnostic sensitivity and specificity as anti-CCP antibodies.[18, 19, 20]

Antibodies against carbamylated proteins (proteins comprising a homo-citrulline residue) have also been described to occur in the serum of patients with RA.[28, 29] Homocitrulline was found to be present in rheumatoid nodule, together with citrulline,[28] and antibodies against carbamylated proteins were found to predict joint damage.[29]

Two serological point-of-care tests (POCT) for the early detection of RA have been very recently developed. The Rheuma-Chec test (Orgentec, Mainz, Germany) combines two biomarkers for the diagnosis of RA—rheumatoid factor and antibodies to MCV. Antibodies to CCP are detected with the CCPOINT™ assay (Euro-Diagnostica, Malmö, Sweden).[25] The tests require only a single drop of whole blood and any general physician can perform them within minutes.

Despite the above advances, there is still room for improvement of the existing serological tests for rheumatoid arthritis, in particular, with respect to sensitivity, specificity and ease of handling.

BRIEF SUMMARY

Surprisingly, it has now been found that patients with rheumatoid arthritis (RA) produce antibodies against citrullinated antibodies. This allows for the manufacture of new diagnostic tests in a variety of formats.

The disclosure, therefore, relates to an antibody comprising a citrulline residue. The disclosure also relates to the diagnostic use of such an antibody, for instance, as an antigen to determine the presence of anti-citrullinated antibodies (ACA) in the circulation of patients with RA or subjects that are predisposed to develop RA. The disclosure is, therefore, also directed toward a method for predicting whether a subject has or will develop RA.

BRIEF DESCRIPTION OF THE DRAWING

FIG. 1: ELISA assay results. Sera from normal control subjects (n=7) and from RA patients that did not have rheumatoid factor (n=7) were tested in a 1:100 dilution in an ELISA assay with immobilized citrullinated rabbit IgG antibodies as antigen.

DETAILED DESCRIPTION

It was found that patients with rheumatoid arthritis (RA) produce antibodies specifically directed against antibodies comprising citrulline or homo-citrulline residues. These antibodies will be referred to herein as citrullinated antibodies.

Citrullinated antibodies were prepared in two ways. First, citrullinated antibodies were prepared by subjecting a purified preparation of rabbit IgG to treatment with peptidylarginine deiminase (PAD, EC 3.5.3.15). This enzyme catalyzes the conversion of protein-bound arginine to citrulline.[27] Citrullinated antibodies were also prepared by chemical carbamylation. In this process, lysine residues present in an antibody are converted into a homo-citrulline residue. Citrullinated rabbit IgG antibodies were thereby obtained (Examples 1 and 2).

As defined herein, the term "antibodies" is used to refer to a specific binding molecule such as a protein, or parts thereof, that are capable of specifically binding to a target compound, usually referred to as an antigen.

Preferred examples of such specific binding molecules are polypeptides or proteins or parts thereof, such as single-chain variable fragments (scFvs), fragment antigen binding regions (Fabs), single-domain antibodies (sdabs), also known as VHH antibodies, nanobodies (camelid-derived single-domain antibodies), or shark IgNAR-derived single-domain antibody fragments called VNAR, or other active components thereof such as proteinaceous aptamers. In an alternative embodiment, a specific binding molecule is a fusion protein comprising the antigen-binding domain of an antibody.

In functional language, the term "antibodies" or "antibody" refers to a protein or polypeptide capable of specific binding to a target molecule often referred to as "antigen." Antibodies (also known as immunoglobulins) are preferably gamma globulin proteins that are found in blood or other bodily fluids of vertebrates, and are used by the immune system to identify and neutralize foreign objects, such as bacteria and viruses.

Naturally occurring human antibodies are typically made of basic structural units—each with two large heavy chains and two small light chains—to form, for example, monomers with one unit, dimers with two units or pentamers with five units.

Antibodies are produced by a kind of white blood cell called a B cell. There are several different types of antibody heavy chain, and several different kinds of antibodies, which are grouped into different isotypes based on which heavy chain they possess. Five different antibody isotypes that perform different roles are known in mammals, and help direct the appropriate immune response for each different type of foreign object they encounter. Some animal species such as camelids (e.g., llamas) and sharks may have aberrant antibody structures.

Although the general structure of all antibodies is very similar, a small region at the tip of the protein is extremely variable, allowing millions of antibodies with slightly different tip structures to exist. This region is known as the hypervariable region. Each of these variants can bind to a different target, known as an antigen. This huge diversity of antibodies allows the immune system to recognize an equally wide diversity of antigens. The unique part of the antigen recognized by an antibody is called an epitope. These epitopes bind with their antibody in a highly specific interaction that allows antibodies to identify and bind only their unique antigen in the midst of the millions of different molecules that make up an organism. Recognition of an antigen by an antibody tags it for attack by other parts of the immune system. Antibodies can also neutralize targets directly, for example, by binding to a part of a pathogen that it needs to cause an infection.

The large and diverse population of antibodies is generated by random combinations of a set of gene segments that encode different antigen binding sites (or paratopes), followed by random mutations in this area of the antibody gene, which create further diversity. Antibody genes also re-organize in a process called "class switching" that changes the base of the heavy chain to another, creating a different isotype of the antibody that retains the antigen-specific variable region. This allows a single antibody to be used in several different isotypes by several different parts of the immune system.

The term "antibody" as used herein, therefore, explicitly includes single-chain antibodies, fragment antigen binding regions, recombinantly produced antibodies, monoclonal antibodies, nanobodies, single-domain antibodies, and the like.

The term "or part thereof" in the context of an antibody or other specific binding molecule is meant to refer to the part of the antibody or specific binding molecule that makes up the specific binding site of the antibody or specific binding molecule and may be interpreted as the part of an antibody or specific binding molecule that is still capable to react with the same epitope as the entire antibody or specific binding molecule from which the fragment was derived.

All kind of specific binding molecules, and derivatives thereof such as antibodies, fusion proteins comprising a specific binding domain of an antibody, antibody fragments, single-domain antibody fragments, other proteinaceous binding domains such as anticalins, and small molecules that specifically bind citrullinated epitopes can be used in the disclosure.

The term "antibodies specifically reactive with a citrullinated epitope" or the like are to be interpreted as an antibody that specifically reacts with a citrulline residue or a homo-citrulline residue in the context of a larger structure such as a polypeptide or a peptide or a peptide nucleic acid or a proteinaceous aptamer or a peptide mimicking structure but that does not react with a similar structure wherein the citrulline residue is replaced by an arginine residue.

Citrulline is an amino acid that is not incorporated into proteins during translation, however, it can be generated by post-translational modification of an arginine residue by peptidylarginine deiminase (PAD).

Citrullination is the post-translational conversion of arginine residues to citrulline residues, which is catalyzed by peptidylarginine deiminase (PAD). Peptidylarginine deiminase (PAD; EC 3.5.3.15) enzymes catalyze the conversion of arginine residues to citrulline residues in proteins. No tRNA exists for citrulline, the presence of citrulline residues in proteins is exclusively the result of post-translational modification. In mammals (humans, mice and rats) five PAD isotypes (PAD1-PAD6; 'PAD4' and 'PAD5' are used for the same isotype), each encoded by a distinct gene, have been identified (Vossenaar et al., *Bioessays* 25:1106-1118, 2003). All these enzymes rely strongly on the presence of Ca2+ for activity and are unable to convert free L-arginine into free L-citrulline. Free L-arginine can be converted to free L-citrulline by nitric oxide synthase (EC 1.14.13.39) in eukaryotes or by arginine deiminase (EC 3.5.3.6) in bacteria. These enzymes are not Ca2+ dependent. Microbial PAD enzymes are preferred. PAD enzymes from *Porphyromonas gingivalis* en *Fusarium graminearum* are particularly preferred. Such enzymes have been described to be expressed in heterologous expression systems, such as *Aspergillus niger* (EP 2032697 A1).

The most pronounced difference between the highly homologous PAD enzymes is their tissue-specific expression. In epidermis PAD1 (synonyms: PAD I, PAD type I) is involved in the citrullination of keratin filaments during the final stages of keratinocyte differentiation, which is important for the reorganization of the cornified envelope. Another site of citrullination in the epidermis is the hair follicle, which contains PAD3 (synonyms PAD III, PAD type III) and its natural substrate trichohyalin (THH). THH is a major structural protein of the inner root sheath cells and the medulla layer of the hair follicle and, to a lesser extent, of other specialized epithelia. The most recently identified PAD isotype, PAD6 (synonym: ePAD), was found in cytoplasmic sheets of mouse oocytes, which play an important role in early embryogenesis. The expression of its human orthologue was found to be restricted to ovary, testis and peripheral blood leukocytes (Chavanas et al., *Gene* vol. 330:19-27, 2004). Originally, this PAD isotype was designated ePAD, but based upon the systematic numbering of other PADs, this isotype was renamed PAD6 (Vossenaar et al., *Bioessays* vol. 25:1106-1118, 2003). The most widely expressed isotype, PAD2 (synonyms PAD II, PAD type II, PAD-H19), is present in many different tissues, like skeletal muscle, brain, spleen, secretory glands and macrophages. Despite this broad expression pattern, only myelin basic protein (MBP) and vimentin have been identified as natural substrates. In multiple sclerosis (MS), patients develop an autoimmune response against MBP. MBP is an abundant protein of the myelin sheath, and its citrullination occurs during development of the central nervous system. Citrullination of vimentin was observed during calcium-ionophore-induced apoptosis of human and mouse macrophages and, as described above, citrullinated vimentin was shown to be the target of the RA-specific anti-Sa autoantibodies. In contrast to the PADs discussed above, which are all mainly localized in the cytoplasm of cells, the PAD4 isotype (synonyms: PAD IV, PAD type IV, HL-60 PAD, PAD V, PAD type V, PADI4) is localized in the nucleus. The nuclear localization signal of PAD4 was found in the N-terminal region of the protein. PAD4 is mainly expressed in peripheral blood granulocytes and monocytes. Substrates of PAD4 in the nucleus are histone core proteins (H2A, H3 and H4) and nucleophosmin/B23, a nucleolar protein that functions in ribosome assembly, nucleocytoplasmic transport and centrosome duplication.

Citrullinated immunoglobulins or antibodies may also be obtained chemically, by converting a lysine residue into a homocutrullin residue. This process is often referred to as carbamylation (Example 2).

The citrullinated antibodies as described in Example 1 or 2 were immobilized on a solid support and it was determined in an ELISA assay as prepared in Example 3 whether blood samples obtained from patients with RA contained antibodies specifically reactive with citrullinated epitopes on citrullinated antibodies.

It was found that serum from patients with RA contained antibodies that were specifically reactive with citrullinated antibodies, in particular, IgG. For that purpose, seven patients with RA that did not contain Rheumatoid Factor in their serum were selected. When the serum obtained from these patients was tested in the ELISA assay of Example 3, six out of seven patients (86%) appeared to have circulating antibodies directed against citrullinated IgG (FIG. 1). These six patients did not have antibodies against non-citrullinated IgG, and neither were anti-citrullinated antibodies (ACA) found in seven randomly selected normal human sera.

It was concluded that citrullinated antibodies are a useful reagent for the detection of RA-specific autoantibodies. In one aspect, the disclosure is, therefore, directed toward an antibody comprising a citrulline residue.

Such antibodies may be obtained from any species as described above. Preferably, the antibody is a vertebrate antibody, such as a mammalian antibody, such as a rabbit, mouse or rat antibody, even more preferably an IgG antibody, a Fab fragment thereof or a nanobody. Citrullinated human IgG antibodies may also be used; however, this is not preferred in certain assay formats. For instance, citrullinated human IgG antibodies may cause non-specific background reactions in an indirect ELISA assay as described herein, by cross-reacting with the labeled anti-human IgG antibody used for the detection of ACA antibodies.

Furthermore, the disclosure is directed toward a method for the detection of antibodies specific for rheumatoid arthritis in a sample from a subject, wherein the sample is contacted with a citrullinated antibody and wherein it is determined whether the sample comprises antibodies specifically reactive with the citrullinated antibody.

As used herein, the term "specifically reactive with" refers to an immune reaction wherein a first antibody from an individual with RA reacts with a citrullinated epitope present on a second antibody, whereas the first antibody does not react with the second antibody when the citrulline residue in the epitope is replaced by an arginine residue.

The specific reactivity of the ACA as described herein should not be confused with rheumatoid factor (RF). Rheumatoid factor (RF) is an autoantibody against the Fc portion of IgG. RF and IgG may join to form immune complexes that contribute to the disease process. Rheumatoid factor can also be a cryoglobulin (antibody that precipitates on cooling of a blood sample); it can be either a monoclonal or a polyclonal IgM. Rarely, other isotypes are found, such as IgA, IgG, IgE and IgD. Rheumatoid Factor, however, does not specifically react with ACA since RF does not discriminate between normal, non-citrullinated antibodies and citrullinated antibodies. Moreover, RF is directed against IgG, whereas ACA are directed against citrullinated antibodies of every isotype.

In a preferred method according to the present invention, care is taken that RF does not interfere with the results of the analysis. This may be performed in a vast number of ways, known to the skilled person.

The interference of RF in a method according to this disclosure may, for example, be prevented by performing a control that detects binding of antibodies not specifically directed against a citrullinated epitope. The control values may then be subtracted from the values obtained in a method as described above.

In an alternative embodiment, binding of RF to the citrullinated antibody may be avoided. For example, the citrullinated antibody used in the method may be selected in such a way that it does not react with RF. Such may, for example, be achieved by using citrullinated Fab fragments that lack the Fc portion of the IgG molecule. In an alternative embodiment, the citrullinated antibody may be of IgM, IgA, IgE or IgD isotype.

In a further alternative arrangement, the citrullinated antibody may be of a non-human origin, such as a recombinant antibody, such as a single-domain antibody.

As used herein, the term "single-domain antibody" refers to antibody-derived proteins that contain the unique structural and functional properties of naturally occurring heavy-chain antibodies. The technology was originally developed following the discovery that camelidae (camels and llamas) possess fully functional antibodies that lack light chains. These heavy-chain antibodies contain a single variable domain (VHH) and two constant domains (CH2 and CH3). Importantly, the cloned and isolated VHH domain is a perfectly stable polypeptide harboring the full antigen-binding capacity of the original heavy-chain antibody.

A single-domain antibody (sdAb, also called Nanobody by Ablynx, the developer) is an antibody fragment consisting of a single monomeric variable antibody domain. Like a whole antibody, it is able to bind selectively to a specific antigen. With a molecular weight of only 12-15 kDa, single-domain antibodies are much smaller than common antibodies (150-160 kDa), which are composed of two heavy protein chains and two light chains, and even smaller than Fab fragments (~50 kDa, one light chain and half a heavy chain) and single-chain variable fragments (~25 kDa, two variable domains, one from a light chain and one from a heavy chain).

Cartilaginous fishes also have heavy-chain antibodies (IgNAR, "immunoglobulin new antigen receptor") from which single-domain antibodies called VNAR fragments can be obtained. An alternative approach is to split the dimeric variable domains from common immunoglobulin G (IgG) from mammalians such as rabbits, mouse, rats or humans into monomers. Although most research into single-domain antibodies is currently based on heavy-chain variable domains, nanobodies derived from light chains have also been shown to bind specifically to target epitopes.

A single-domain antibody is a peptide chain of about 110 amino acids long, comprising one variable domain (VH) of a heavy-chain antibody, or of a common IgG. These peptides have similar affinity to antigens as whole antibodies, but are more heat-resistant and stable toward detergents and high concentrations of urea. Those derived from camelid and fish antibodies are less lipophilic and more soluble in water, owing to their complementarity-determining region 3 (CDR3), which forms an extended loop covering the lipophilic site that normally binds to a light chain. In contrast to common antibodies, some single-domain antibodies are heat-resistant up to 90 degrees Celsius.

In a further alternative embodiment, the sample from the subject to be tested may be depleted from RF, or RF may be inactivated prior to testing. For that purpose, specific IgM blockers are commercially available. The skilled person is well aware of the diversity of methods that may be employed to prevent the interference of RF with the presently disclosed method.

In a preferred embodiment of such a method, the citrullinated antibody is immobilized on a solid support. There are numerous ways of performing such a method, and the skilled person is well aware of the various solid supports, which all have their specific advantages and disadvantages. The solid support may advantageously be chosen from the group consisting of glass, nitrocellulose, polystyrene, paper or any other kind of commercially available support. In a particularly preferred embodiment, the solid support is polystyrene such as, for example, an ELISA plate. In a further preferred embodiment, the disclosure relates to a method performed in an ELISA assay format.

The discovery that patients with RA produced antibodies against citrullinated antibodies (ACA) allowed the preparation of assay formats that have specific advantages over the assays described in the prior art.

In a method according to a preferred embodiment of the disclosure, a citrullinated antibody is attached to a red blood cell. That may be done by incubating red blood cells with citrullinated antibodies with random specificity, such as IgG antibodies or antibodies of any other isotype. It may also be done in a specific way, namely, by using citrullinated antibodies that are specifically reactive with a component of the outer cell surface of a red blood cell.

For example, citrullinated antibodies that were directed against glycophorin A, a component of the outer cell surface of a red blood cell, were prepared. Example 1 shows the exact details of the antibodies and its citrullination using PAD.

The term "a component of the outer cell surface of a red blood cell" is used herein to indicate an antigenic determinant expressed at the outside of a red blood cell. There are currently over 300 red blood cell surface antigenic determinants recognized by the International society of Blood transfusion. Most of these belong to 1 of 29 blood group systems (G. Daniels, *ISBT Science Series* 1:3-8 (2006). The MNS antigen system is a human blood group system based upon two genes (glycophorin A and glycophorin B) on chromosome 4.

Alternative and/or preferred outer cell surface components are listed in Table 1 of Daniels (supra) and include Urea transporter (UT)-B, Aquaporin 1, Aquaporin 3, CD233, CD241, CD240D, CD240CE, Xk protein, CD234, CD329, CD242, ERMAP, CD147, CD47, CD55, CD59, CD35, CD44, CD99, CD108, CD151, Acetylcholesterinase, CD238, CD297, CD236C, CD236D, CD235A and CD235B.

Glycophorins A (GYPA) and B (GYPB) are preferred therein and are major sialo-glycoproteins of the human erythrocyte membrane that bear the antigenic determinants for the M, N and Ss blood groups. In addition to the M or N and S or s antigens that commonly occur in all populations, about 40 related variant phenotypes have been identified. These variants include all the variants of the Miltenberger complex and several isoforms of Sta; also, Dantu, Sat, He, Mg, and deletion variants Ena, S-s-U- and Mk. Most of the variants are the result of gene recombinations between GYPA and GYPB. [World Wide Web at ncbi.nlm.nih.gov/gene?Db=gene&Cmd=ShowDetailView& TermToSearch=29931.]

Antibodies against human glycophorin A are commercially available, for instance, from BioLegend (World Wide Web at biolegend.com/pacific-blue-anti-human-cd235a-glycophorin-a-antibody-7880.html), from Abcam, Cambridge, UK, or from Antibodies Online, ABIN337240, a rabbit polyclonal IgG antibody, directed against the N-terminal part of GlycA. Nanobodies specific for glycophorin A have also been described.[30]

The citrullinated glycophorin A antibodies obtained according to the procedure outlined in Example 1 allowed us to determine the presence of antibodies against citrullinated antigens (ACA) in samples obtained from RA patients using a hemagglutination assay format (Example 4).

In one of its embodiments, the disclosure, therefore, relates to a method as described above wherein the detection occurs in a hemagglutination assay.

In more detail, the disclosure relates to a method as described above comprising the steps of: a) providing a citrullinated antibody, b) providing a sample comprising antibodies from a subject, c) providing red blood cells, d) contacting the citrullinated antibody with the sample and the red blood cells and e) detecting whether agglutination of the red blood cells occurs, wherein agglutination indicates the presence of anti-citrullinated antibodies specific for rheumatoid arthritis in the sample.

Step d) of the above method should not be so narrowly construed that the contacting of the citrullinated antibody with the sample and the red blood cells should necessarily be done at the same time. The method works well if the citrullinated antibody is contacted with the red blood cells first and only thereafter with the sample containing the antibodies against the citrullinated antibody (ACA). From a perspective of efficiency of use, however, it is preferred that the contacting takes place simultaneously or approximately at the same time.

The term "approximately at the same time" in this context means with an interval of less than 5 minutes, such as less than 4 minutes, or 3, 2 or even 1 minute.

In a further preferred embodiment, the disclosure relates to an agglutination assay wherein autologous red blood cells are used. In other words, the disclosure relates to a method as described above wherein the antibodies from step b) and the red blood cells from step c) are comprised in the same sample. In a further preferred embodiment, the red blood cells are from the subject.

Such an autologous agglutination assay was developed and samples from the seven RA patients described above were tested. The results of the autologous agglutination assay confirmed the results obtained with the ELISA assay (Table 1).

TABLE 1

Autologous agglutination assay with seven RA sera.

|  | Positive | Negative |
|---|---|---|
| Rheumatoid arthritis | 6 | 1 |
| Normal control | 0 | 7 |

It was found that more than 80% of patients with rheumatoid arthritis had ACA circulating in their blood. None of the control patients tested had such antibodies. It was concluded that ACA is a reliable and very sensitive and specific marker antibody for RA.

Without wishing to be bound by theory, it is thought that the citrullinated GlycA antibodies cover the red blood cells with citrullinated epitopes, thereby making the red blood cells targets for ACA present in the serum and blood of RA patients. When ACA antibodies are present, the red blood cells will agglutinate. In the autologous agglutination assay, the red blood cells of the RA patient become covered by citrullinated epitopes and the patient's own antibodies will cause the red blood cells to agglutinate if ACAs are present in the blood.

In a prospective study, it was found that a large number of subjects that had no clinical signs of rheumatoid arthritis but were about to develop rheumatoid arthritis within a period of 10 years, also had ACA in circulation. It was concluded that ACA is a marker for the prognosis of RA.

EXAMPLES

Example 1

Preparation of Citrullinated IgG

Rabbit IgG (25 µg) was citrullinated in vitro by rabbit skeletal muscle PAD (75 mU; Sigma-Aldrich; EC 3.5.3.15) in deimination buffer (40 mM Tris-HCl, pH 7.5, 5 mM CaCl2 and 1 mM DTT) and incubated at 37° C. for 3 hours. The reaction was stopped by the addition of EGTA, pH 8.0, to a concentration of 50 mM. Citrullinated rabbit IgG was obtained after dialysis overnight against 10 mM Tris pH 7.6 with 2 mM EDTA.

Goat Glycophorin A antibodies (25 µg) obtained from Abcam, UK, were citrullinated in vitro by rabbit skeletal muscle PAD (75 mU; Sigma-Aldrich; EC 3.5.3.15) in deimination buffer (40 mM Tris-HCl, pH 7.5, 5 mM CaCl2 and 1 mM DTT) and incubated at 37° C. for 3 hours. The reaction was stopped by the addition of EGTA, pH 8.0, to a concentration of 50 mM. Citrullinated goat IgG was obtained after dialysis overnight against 10 mM Tris pH 7.6 with 2 mM EDTA.

Another Glycophorin A antibody was obtained from Santa Cruz Biotechnology. R10 sc-53905 is a monoclonal IgG1 mouse antibody directed against the extracellular domain of Glycophorin A. This antibody was citrullinated in vitro by rabbit skeletal muscle PAD (75 mU; Sigma-Aldrich; EC 3.5.3.15) in deimination buffer (40 mM Tris-HCl, pH 7.5, 5 mM CaCl2 and 1 mM DTT) and incubated at 37° C. for 3 hours. The reaction was stopped by the addition of EGTA, pH 8.0, to a concentration of 50 mM. Citrullinated mouse IgG was obtained after dialysis overnight against 10 mM Tris pH 7.6 with 2 mM EDTA.

A parallel incubation of a species-matched IgG preparation to which no PAD enzyme was added served as a negative control.

Example 2

Preparation of Carbamylated IgG

Carbamylated IgG was obtained by incubating 1.18 mg rabbit IgG dissolved in 1 mL PBS with 1 mL of a 0.2 M KCNO in 0.1 M Na2HPO4-buffer for three hours at 37° C. Carbamylated IgG was then dialyzed against 0.9% NaCl overnight at 4 degrees Celsius and stored until use at 4 degrees Celsius. This IgG was used as an antigen in an ELISA assay for the detection of anti-citrullinated antibodies in sera from patients with RA. Non-carbamylated IgG was therein used as a control.

Example 3

ELISA with Citrullinated Antibodies

An ELISA assay for the detection of antibodies against citrullinated antibodies was developed as follows. Citrullinated IgG prepared as described above was immobilized on NUNC ELISA plates by incubating 50 microliters per well of 100 micrograms per milliliter citrullinated IgG at 37° C. overnight. Residual binding sites were blocked by adding 50 microliters of 100 micrograms per milliliter Bovine Serum Albumin (BSA) in phosphate buffered saline (PBS) to each well of the microtiter plate and incubating for 1 hour at 37°

C. The plates were then washed three times with PBS+ 0.05% TWEEN® 20 (PBS/TWEEN®) and stored dry at 4° C. if not immediately used.

Control plates were prepared in exactly the same way, except that the control plates contained non-citrullinated antibodies from species-matched controls immobilized to the solid phase.

Serial dilutions (1/10 to 1/100,000) of human serum from RA patients known to be negative for rheumatoid factor were used to investigate the presence of antibodies against citrullinated IgG. Fifty microliters of each serial dilution was filled into a well of the microtiter plate and incubated at 37° C. for 3 hours. After washing three times with PBS/TWEEN®, 50 microliters of a 1:1000 dilution of rabbit horse radish peroxidase labeled anti-human IgG in PBS was added and incubated for 2 hours at 37° C. After washing three times with PBS/TWEEN®, 100 microliters of TMB was added to each well and the plates were incubated in the dark at 37° C. for 30 minutes. The reaction was stopped by adding 50 microliters of 2 M H2SO4 to each well and the absorbance was read at 450 nm with a TITERTEK® multiscan (Flow Laboratories, Irvine UK).

Representative results obtained with citrullinated rabbit IgG are shown in FIG. 1. Other citrullinated immunoglobulins as described above yielded comparable results.

Example 4

Hemagglutination Assay

Autologous agglutination tests were performed on a glass cover slip by mixing 50 microliters of either patient blood or control blood with 50 microliters of PBS containing 0.1% BSA with or without 20 micrograms per milliliter of citrullinated glycophorin A antibody. The mixture was spread over the glass surface to a circle with a diameter of about 1 centimeter and agglutination was visually evaluated after 2 minutes.

REFERENCES

1. Dörner T., K. Egerer, E. Feist, and G. R. Burmester. Rheumatoid factor revisited. *Curr. Opin. Rheumatol.* 2004; 16:246-253.

2. Arnett F. C., S. M. Edworthy, and D. A. Bloch, et al. The American Rheumatism Association 1987 revised criteria for the classification of rheumatoid arthritis. *Arthritis Rheum.* 1988; 31:315-324.

3. Schur P. H. Anti-cyclic citrullination peptide antibodies: diagnostic, predictive and monitoring value in RA. *Int. J. Adv. Rheumatol.* 2005; 3:77-83.

4. Van Venrooij W. J., and G. J. Prujin. Citrullination; a small change for a protein with great consequences for rheumatoid arthritis. *Arthritis Res.* 2000; 2:249-251.

5. Yoiinou P., and G. Serre. The anti-perinuclear factor and antikeratin antibody systems. *Int. Arch. Allergy Immunol.* 1995; 107:508-518.

6. Schellekens G. A., B. A. de Jong, F. H. van den Hoogen, L. B. van de Putte, and W. J. van Venrooij. Citrulline is an essential constituent of antigenic determinants recognized by rheumatoid arthritis-specific autoantibodies. *J. Clin. Invest.* 1998; 101:273-281.

7. Schellekens G. A., H. Visser, and B. A. de Jong, et al. The diagnostic properties of rheumatoid arthritis antibodies recognizing a cyclic citrullinated peptide. *Arthritis Rheum.* 2000; 43:155-163.

8. van Venrooij W. J., A. J. Zendman, and G. J. Pruuijn. Autoantibodies to citrullinated antigens in (early) rheumatoid arthritis. *Autoimmun. Rev.* 2006; 6:37-41.

9. van Venrooij W. J., J. M. Hazes, and H. Visser. Anticitrullinated protein/peptide antibody and its role in the diagnosis and prognosis of early rheumatoid arthritis. *Neth. J. Med.* 2002; 60:383-388.

10. Coenen D., P. Verschueren, R. Westhovens, and X. Bossuyt. Technical and diagnostic performance of six assays for the measurement of citrullinated protein/peptide antibodies in the diagnosis of rheumatoid arthritis. *Clin. Chem.* 2007; 53:498-504.

11. Bizzara N., E. Tonutti, R. Tozzoli, and D. Villalta. Analytical and diagnostic characteristics of 11 $2^{nd}$- and 3rd-generation immunoenzymatic methods for the detection of antibodies to citrullinated proteins. *Clin. Chem.* 2007; 53:1527-1533.

12. Sebbag M., N. Moinard, I. Auger, et al. Epitopes of human fibrin recognized by the rheumatoid arthritis-specific autoantibodies to citrullinated proteins. *Eur. J. Immunol.* 2006; 36:2250-2263.

13. Vander Cruyssen B., T. Cantaert, L. Nogueira, et al. Diagnostic value of anti-human citrullinated fibrinogen ELISA and comparison with four other anti-citrullinated protein assays. *Arthritis Res. Ther.* 2006; 8

14. Nielen M. M., A. R. van der Horst, D. van Schaardenburg, et al. Antibodies to citrullinated human fibrinogen (ACF) have diagnostic and prognostic value in early arthritis. *Ann. Rheum. Dis.* 2005; 64:1199-1204.

15. Kinloch A., V. Tatzer, R. Wait, et al. Identification of citrullinated alpha-enolase as a candidate autoantigen in rheumatoid arthritis. *Arthritis Res. Ther.* 2005; 7:R1421-R1429.

16. Saulot V., O. Vittecoq, R. Charlionet, et al. Presence of autoantibodies to the glycolytic enzyme alpha-enolase in sera from patients with early rheumatoid arthritis. *Arthritis Rheum.* 2002; 46:1196-1201.

17. Vossenaar E. R., N. Despres, E. Lapointe, et al. Rheumatoid arthritis specific anti-Sa antibodies target citrullinated vimentin. *Arthritis Res. Ther.* 2004; 6:R142-R150.

18. Bang H., K. Egerer, A. Gauliard, et al. Mutation and citrullination modifies vimentin to a novel autoantigen for rheumatoid arthritis. *Arthritis Rheum.* 2007; 56:2503-2511.

19. Dejaco C., W. Klotz, H. Larcher, C. Duftner, M. Schirmer, and M. Herold. Diagnostic value of antibodies against a modified citrullinated vimentin in rheumatoid arthritis. *Arthritis Res. Ther.* 2006; 8

20. Soós L., Z. Szekanecz, and Z. Szabo, et al. Clinical evaluation of anti-mutated citrullinated vimentin by ELISA in rheumatoid arthritis. *J. Rheumatol.* 2007; 34:1658-1663.

21. Usum J., M. M. Nielen, D. van Schaardenburg, et al. Antibodies to mutated citrullinated vimentin and disease activity score in early arthritis: a cohort study. *Arthritis Res. Ther.* 2008; 10.

22. Innala L., H. Kokkonen, and C. Eriksson, et al. Antibodies against mutated citrullinated vimentin are a better predictor of disease activity at 24 months in early rheumatoid arthritis than antibodies against citrullinated peptides. *J. Rheumatol.* 2008; 35:1002-1008.

23. Mathsson L., M. Mullazehl, M. C. Wick, et al. Antibodies against citrullinated vimentin in rheumatoid arthritis. *Arthritis Rheum.* 2008; 58:36-45.

24. Feist E., K. Egerer, and G. R. Burmester. Autoantikörperprofile bei der rheumatoi den Arthritis. *Z. Rheumatol.* 2007; 66:212-218.

25. Snijders G. F., A. A. den Broeder, K. Bevers, et al. Measurement characteristics of a new rapid anti-CCP2 test compared to the anti-CCP2 ELISA. *Scand. J. Rheumatol.* 2008:151-154.

26. Egerer et al., *Dtsch Arztebl* 2009; 106 (10); 159-163.

27. Vossenaar et al., *Bioessays* 2003; 25(11):1106-18.

28. Turunen et al., *J. Translational Medicine* 2013; 11: 224-229.

29. Shi et al., *Proc. Natl. Acad. Sci. U.S.A.* 2011; 42: 17372-17377.

30. Habib et al., *Anal. Biochem.* 2013; 438: 82-89.

The invention claimed is:

1. A method for the detection of first antibodies specific for a second antibody comprising a citrulline residue, the method comprising:
   providing the second antibody comprising a citrulline residue, wherein the second antibody is citrullinated in vitro by contacting a non-citrullinated second antibody with an enzyme of EC 3.5.3.15,
   contacting a sample from a subject suffering from rheumatoid arthritis with the second antibody comprising a citrulline residue to form a complex; and
   detecting the complex comprising detecting specific binding between the first antibody and the second antibody comprising the citrulline residue;
   wherein the sample comprises the first antibody, and wherein the first antibody does not bind the non-citrullinated second antibody.

2. The method according to claim 1, wherein the second antibody comprising the citrulline residue is directed against a component of the outer cell surface of a red blood cell.

3. The method according to claim 2, wherein the second antibody comprising the citrulline residue is reactive with glycophorin.

4. The method according to claim 3, wherein the glycophorin is glycophorin A.

5. The method according to claim 1, wherein the second antibody comprising the citrulline residue is immobilized on a solid support.

6. The method according to claim 5, wherein the solid support is a nitrocellulose membrane.

7. The method according to claim 5, wherein the solid support is a polystyrene support.

8. The method according to claim 1, wherein the formation of the antibody complex occurs as part of a hemagglutination assay.

9. The method according to claim 1, wherein the enzyme of EC 3.5.3.15 is a PAD2 enzyme.

10. The method according to claim 1, wherein the enzyme of EC 3.5.3.15 is a PAD4 enzyme.

11. A hemagglutination method for the detection of first antibodies specific for a second antibody comprising a citrulline residue, the method comprising:
    providing the second antibody comprising a citrulline residue, wherein the second antibody is citrullinated in vitro by contacting a non-citrullinated second antibody with an enzyme of EC 3.5.3.15,
    providing a sample from the subject suffering from rheumatoid arthritis, wherein the sample comprises the first antibody,
    providing red blood cells,
    contacting the second antibody comprising a citrulline residue with the sample and the red blood cells, and
    detecting agglutination of the red blood cells,
    wherein the first antibody does not bind to the non-citrullinated second antibody.

12. The method according to claim 11, wherein the sample comprising antibodies from the subject suffering from rheumatoid arthritis also comprises the red blood cells.

13. The method according to claim 12, wherein the red blood cells are from the subject suffering from rheumatoid arthritis.

14. The method according to claim 7, wherein the polystyrene support is an ELISA plate.

15. The method according to claim 8, wherein the second antibody comprising the citrulline residue is directed against a component of the outer cell surface of a red blood cell.

16. The method according to claim 8, wherein the second antibody comprising the citrulline residue is reactive with glycophorin.

17. The method according to claim 16, wherein the glycophorin is glycophorin A.

18. The method according to claim 11, wherein the second antibody comprising the citrulline residue is directed against a component of the outer cell surface of a red blood cell.

19. The method according to claim 11, wherein the second antibody comprising the citrulline residue is reactive with glycophorin.

20. The method according to claim 19, wherein the glycophorin is glycophorin A.

* * * * *